United States Patent [19]
Ishikawa et al.

[11] Patent Number: 6,042,608
[45] Date of Patent: Mar. 28, 2000

[54] FIGURE ADJUSTING PAD AND PROCESS FOR MANUFACTURING SAME

[75] Inventors: Suguru Ishikawa; Hiroshi Chiba, both of Shizuoka; Shigeru Koshibe, Yokohama; Tetsuo Miyamura, Ohtsui, all of Japan

[73] Assignees: Kabushiki Kaisha Sigel, Tokyo; Wacoal Corp., Kyoto, both of Japan

[21] Appl. No.: 08/927,406

[22] Filed: Sep. 10, 1997

Related U.S. Application Data

[62] Division of application No. 08/488,499, Jun. 9, 1995, Pat. No. 5,733,335.

[30] Foreign Application Priority Data

Jun. 10, 1994 [JP] Japan ................................ 6-152796

[51] Int. Cl.⁷ .................................................. A61F 2/52
[52] U.S. Cl. ............................ 623/7; 2/267; 450/57
[58] Field of Search ........................ 623/7, 8; 450/57; 156/77–79, 242, 246; 264/46.4, 46.6

[56] References Cited

U.S. PATENT DOCUMENTS

| | | |
|---|---|---|
| 2,526,808 | 10/1950 | Cohen . |
| 2,727,278 | 12/1955 | Thompson . |
| 3,050,734 | 8/1962 | Dopyera . |
| 3,266,495 | 8/1966 | Sachs . |
| 3,801,420 | 4/1974 | Anderson . |
| 4,090,010 | 5/1978 | Warwicker et al. . |
| 4,125,117 | 11/1978 | Lee . |
| 4,212,839 | 7/1980 | Funahashi . |
| 4,380,569 | 4/1983 | Shaw . |
| 4,566,458 | 1/1986 | Weinberg . |
| 4,676,795 | 6/1987 | Grundei ........................ 623/8 |
| 4,681,587 | 7/1987 | Eberl et al. . |
| 4,795,399 | 1/1989 | Davis . |
| 5,098,330 | 3/1992 | Greenberg . |
| 5,106,473 | 4/1992 | Valtakari . |
| 5,165,113 | 11/1992 | Hyams et al. . |
| 5,340,352 | 8/1994 | Nakanishi et al. ................... 450/57 |
| 5,340,362 | 8/1994 | Nakanishi et al. . |
| 5,527,359 | 6/1996 | Nakamura et al. . |

FOREIGN PATENT DOCUMENTS

| | | |
|---|---|---|
| 15223/88 | 11/1989 | Australia . |
| 0 178 483 | 4/1986 | European Pat. Off. . |
| 0 433 636 | 6/1991 | Japan . |

*Primary Examiner*—Bruce E. Snow
*Attorney, Agent, or Firm*—Wenderoth, Lind & Ponack, L.L.P.

[57] ABSTRACT

A figure adjusting pad capable of permitting mold release to be readily carried out, being significantly improved in air-permeability, preventing a wearer from having an unpleasant feeling toward it when it is worn and eliminating ply separation with use. The figure adjusting pad includes a pad body including a foamed layer increased in air-permeability and arranged on a rear side thereof and a silicone gel layer arranged on a front side thereof which are laminated on each other. The pad also includes a cover sheet for covering an outer surface of the pad body, which includes a facing sheet for covering a front side of the pad body and a backing sheet for covering a rear side of the pad body. The facing sheet includes a knitted web increased in stretchability arranged on a front side thereof and a polyurethane film arranged on a rear side thereof and laminated on the knitted web. The backing sheet includes a non-woven fabric or a knitted web increased in air-permeability which is thermally bonded to the foamed layer by means of an air-permeable hot melt. Also, a process for preparing the pad is disclosed.

42 Claims, 10 Drawing Sheets

6,042,608

FIGURE ADJUSTING PAD AND PROCESS FOR MANUFACTURING SAME

This is a divisional of U.S. application Ser. No. 08/488,499, filed Jun. 9, 1995, now U.S. Pat. No. 5,733,335.

BACKGROUND OF THE INVENTION

This invention relates to a figure retaining or adjusting pad and a process for manufacturing the same, and more particularly to a pad for retaining or adjusting the figure of, for example, a woman and a process for manufacturing the same.

When the breast of a woman is excised by operation for, for example, mastitis or the like, a figure or breast adjusting pad made in conformity to the breast is often substituted therefor. Thus, the figure adjusting pad is substituted for a part of the body, therefore, it is desired to exhibit properties similar to those of the body. This requires the figure adjusting pad to have flexibility, elasticity, shape-retention, touch and strength sufficient to conform to the body. Also, the figure adjusting pad is typically fitted directly to the bare skin, resulting in the pad being required to exhibit satisfactory air-permeability and possess aesthetic properties and qualities sufficient to act as a part of a foundation.

In view of the foregoing, a pad made of a gel-like material formed with perforations comprising open cells is proposed, as disclosed in Japanese Utility Model Publication No. 40728/1986. However, the pad proposed is made of an oily or water-containing gel material, resulting in having a sticky surface. Thus, the conventional pad is deteriorated in touch, is decreased in surface strength, and fails to permit the periphery thereof to exhibit satisfactory shape-retention. In order to solve these problems, the gel-like material is fully sealed and covered with a plastic film or the like. Unfortunately, this fails to provide sufficient adhesion between the gel-like material of the pad and the plastic film, leading to peeling or removal of the gel-like material from the plastic film, as well as movement and deformation of the gel-like material and wrinkling of the film.

Also, the conventional pad fails to exhibit sufficient shape-retention, for example, when it is applied to a breast adjusting pad. This is particularly noticeable at the periphery of the pad, so that a final product is highly deteriorated in quality. One of the assignees proposed an approach to the problem of the shape-retention, as suggested in Japanese Patent Application Laid-Open Publication No. 131007/1993, wherein an end of the pad is subjected to a sewing treatment in order to solve the problem.

Also, the assignee attempted to provide a figure adjusting pad with improved fat and weight sensation and increased air-permeability, as proposed in Japanese Patent Application No. 152796/1994, which discloses a figure adjusting pad and a method for preparing the same. In the Japanese application, as shown in FIG. 13(a), a shaping sheet 10' which comprises a sheet 11' made of vinyl chloride is temporarily adhered to a knitted web S by means of a synthetic resin adhesive 12'. Unfortunately, use of the synthetic resin adhesive 12' causes adhesion between the shaping sheet 10' and the knitted web S to be excessively increased to the degree of rendering the release of a protuberance forming mold from a formed pad body 2' (FIG. 13(b)) substantially difficult, resulting in troubles such as retention of the synthetic resin adhesive 12' on the fabric, damage to the fabric S and the like.

Also, as shown in FIG. 13(b), adhesion between a rear surface of the pad body 2' and a backing sheet 3a is carried out by means of an adhesive 23'. The adhesive 23' is applied uniformly over all of a contact region between the pad body 2' and the backing sheet 3a. Thus, the pad body 2' and backing sheet 3a are deteriorated in air-permeability at a region thereof to which the adhesive 23' is applied even when they are formed of an airpermeable material, resulting in the formed figure adjusting pad failing to exhibit satisfactory air-permeability. Further, the backing sheet 3a is contacted directly with the skin of a wearer, thereby causing sensation of the cured adhesive 23' to be carried to the skin, resulting in the wearer having an unpleasant feeling toward the pad. Moreover, joining between a polyurethane film P acting as a facing sheet and the fabric S is carried out by only penetrating the polyurethane film P into stitches of the fabric S accompanied by softening of the film P, so that repeated use of the figure adjusting pad possibly causes peeling of the film P and the fabric S from each other.

SUMMARY OF THE INVENTION

The present invention has been made in view of the foregoing disadvantages of the prior art.

Accordingly, it is an object of the present invention to provide a figure adjusting pad which is capable of permitting mold release to be readily carried out.

It is another object of the present invention to provide a figure adjusting pad which is capable of being significantly improved in air-permeability.

It is a further object of the present invention to provide a figure adjusting pad which is capable of preventing a wearer from having an unpleasant feeling toward it when it is worn.

It is still another object of the present invention to provide a figure adjusting pad which is capable of eliminating ply separation with use.

It is a still further object of the present invention to provide a process for manufacturing a figure adjusting pad which is capable of providing a figure adjusting pad exhibiting the above-described properties.

In accordance with one aspect of the present invention, a figure adjusting pad is provided. The pad comprises a pad body including a foamed layer increased in air-permeability and arranged on a wrong side thereof and a silicone gel layer arranged on a right side thereof, which are laminated on each other. The pad also comprises a cover sheet for covering an outer surface of the pad body. The cover sheet includes a facing sheet for covering a front side of the pad body and a backing sheet for covering a rear side of the pad body. The facing sheet includes a knitted web increased in stretchability arranged on a front side thereof and a polyurethane film arranged on a rear side thereof and laminated on the knitted web. The backing sheet includes a non-woven fabric or a knitted web increased in air-permeability which is thermally bonded to the foamed layer by means of an air-permeable hot melt.

In a preferred embodiment of the present invention, the silicone gel layer is formed of a silicone gel having a consistency, as defined by JIS-K2220, within a range between 75 and 105.

In a preferred embodiment of the present invention, the polyurethane film is formed of flexible polyurethane having a hardness, as defined by JIS-K6301, within a range between 65° and 85°.

In a preferred embodiment of the present invention, the foamed layer is formed into an open-cell structure by pressing or crumpling a silicone foam of 10 to 15 in magnification of foaming and 0.1 or less in specific gravity.

In a preferred embodiment of the present invention, the air-permeable hot melt comprises a spidery sheet-like member provided with a plurality of air holes and has a METSUKE weight set to be 10 to 100 g/m$^2$.

In a preferred embodiment of the present invention, the knitted web is formed by subjecting at least one of a natural fiber and a chemical fiber to tricot stitch, raschel stitch, plain stitch, rib stitch or interlock stitch.

In a preferred embodiment of the present invention, the silicone gel layer is formed of a silicone gel having a material decreased in specific gravity added thereto.

In a preferred embodiment of the present invention, the figure adjusting pad further comprises an air-permeable edging fabric arranged on a periphery of the figure adjusting pad. The pad body, facing sheet and backing sheet are bound-seamed together by the edging fabric.

In accordance with another aspect of the present invention, a process for manufacturing a figure adjusting pad is provided. The method comprises a shaping sheet adhering step of adhering a facing sheet and a shaping sheet to each other, a protuberance forming mold forming step of forming the shaping sheet having the facing sheet adhered thereto into a protuberance forming mold of a desired configuration while keeping the facing sheet facing inside, a pad body forming step of forming a pad body including a silicone gel layer and a foamed layer increased in air-permeability into a desired configuration by means of the protuberance forming mold formed, a backing sheet adhering step of adhering a backing sheet to a rear side of the pad body formed, a mold release step of removing the protuberance forming mold from the pad body formed, and a cutting step of removing an extra peripheral portion of the pad body therefrom by cutting. The pad body forming step is carried out by pouring a gel layer stock solution into the protuberance forming mold formed in the protuberance forming mold forming step, pouring a foamed layer stock solution into the gel layer stock solution to form a front side of the pad body and downwardly pressing a foamed layer being cured to concurrently carry out formation of the rear side of the pad body and formation of an open-cell structure of the foamed layer.

In a preferred embodiment of the present invention, the shaping sheet adhering step is carried out by adhering a polyurethane film to one surface of a knitted web increased in stretchability by means of a polyurethane adhesive, laminating the shaping sheet made of a thermoplastic copolyester film on the other surface of the knitted web to provide a laminate, and pressurizing and heating the laminate to form penetration engagement between the shaping sheet and the knitted web. The shaping sheet is partially penetrated into stitches of the knitted web, resulting in the shaping sheet and knitted web adhering to each other.

In a preferred embodiment of the present invention, the backing sheet adhering step is carried out by putting an air-permeable hot melt on the rear side of the pad body formed and arranged in the protuberance forming mold and putting a non-woven fabric or a knitted web increased in air-permeability on the hot melt, followed by pressurizing and heating, leading to adhesion of the backing sheet.

In a preferred embodiment of the present invention, the air-permeable hot melt comprises a spidery sheet-like member provided with a plurality of air holes and has a METSUKE weight set within a range of 10 to 100 g/m$^2$.

In a preferred embodiment of the present invention, the pad body forming step is so carried out that a polyurethane film arranged in the protuberance forming mold is subjected to a primer treatment before pouring of the gel layer stock solution and foamed layer stock solution.

In a preferred embodiment of the present invention, the method further comprises a sewing step of subjecting the periphery of the figure adjusting pad to bound-seaming. The sewing step is carried out by applying an air-permeable edging fabric to a periphery of the figure adjusting pad and subjecting the pad body, facing sheet and backing sheet to bound-seaming together with the edging fabric.

In a preferred embodiment of the present invention, formation of the rear side of the pad body in the pad body forming step takes place by using a recess forming die or a recess forming mold, carrying out pouring of the foamed layer stock solution, putting the recess forming die or recess forming mold on the foamed layer stock solution and pressing the foamed layer stock solution by means of the recess forming die or recess foaming mold.

BRIEF DESCRIPTION OF THE DRAWINGS

These and other objects and many of the attendant advantages of the present invention will be readily appreciated as the same becomes better understood by reference to the following detailed description when considered in connection with the accompanying drawings wherein like reference characters designate like or corresponding parts throughout, and wherein:

FIGS. 13(a) and 13(b) are vertical sectional side elevation views showing a shaping sheet adhering step and a backing sheet adhering step in a process of the present invention, respectively.

DETAILED DESCRIPTION OF THE PREFERRED EMBODIMENTS

Now, the present invention will be detailedly described hereinafter with respect to the accompanying drawings.

Figure 1A:
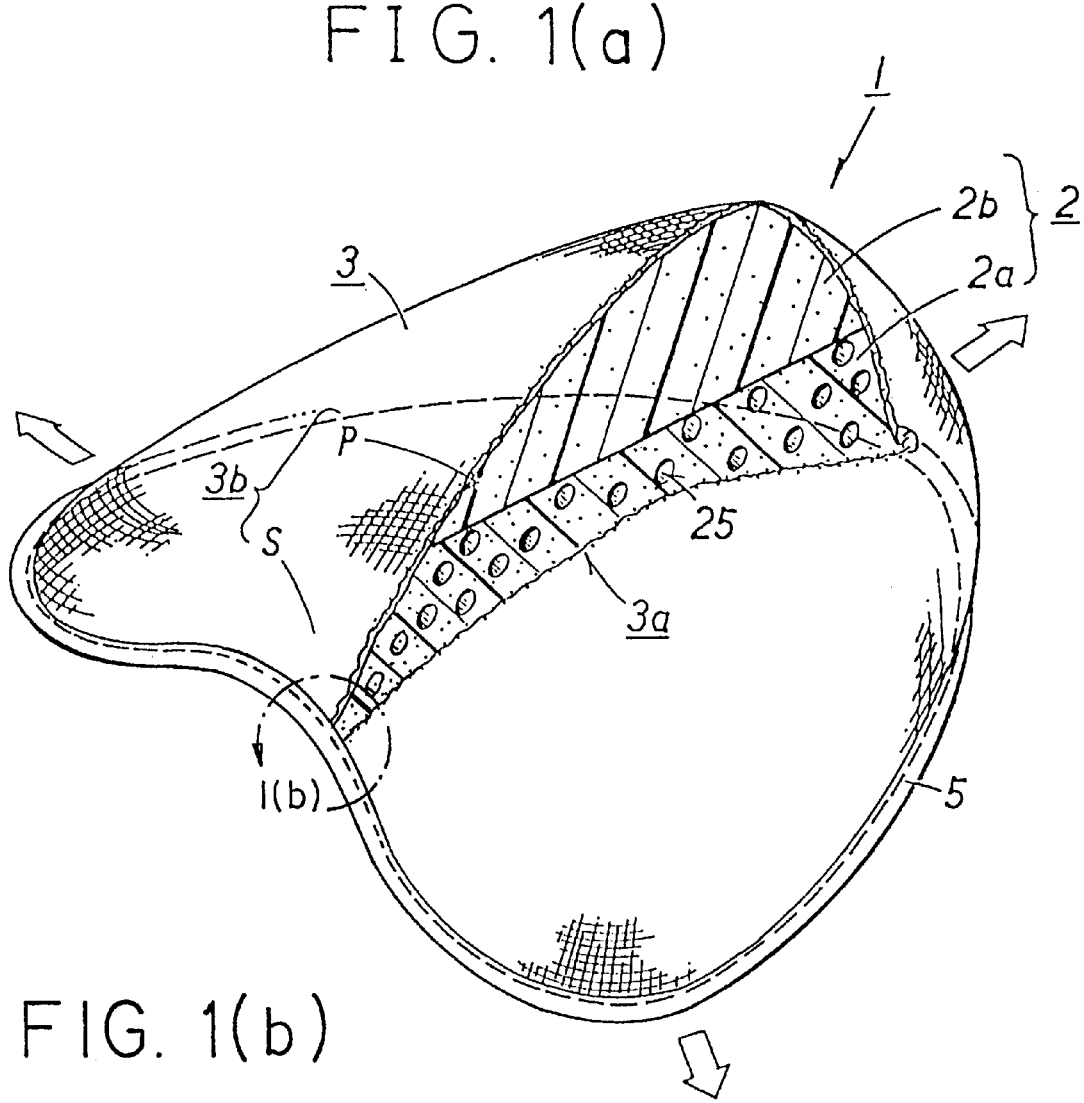
FIG. 1 is a partially cutaway perspective view showing an embodiment of a figure adjusting pad according to the present invention, which is in the form of a breast adjusting pad.
Figure 1B:
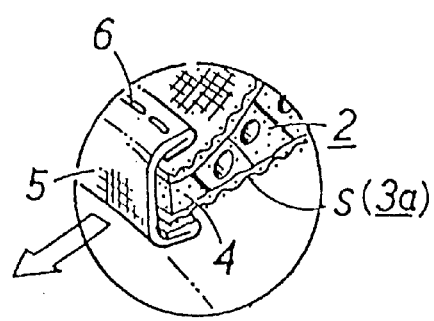

Referring first to FIG. 1, an embodiment of a figure adjusting pad according to the present invention is illustrated. A figure adjusting pad of the illustrated embodiment is generally designated by reference numeral 1, and is in the form of a breast adjusting pad by way of example. The figure adjusting pad 1 generally includes a pad body 2 having a front side expanded into a convex shape and a rear side formed into a substantially concave shape and a cover sheet 3 applied to an outer surface of the pad body 2.

The pad body 2 includes an air-permeable foamed layer 2a arranged on a wrong (back) side of the figure adjusting pad which faces the skin of a wearer and a silicone gel layer 2b arranged on a right (front) side of the figure adjusting pad which is opposite to the wrong side. The foamed layer 2a and silicone gel layer 2b may be laminated on each other. The cover sheet 3 includes a backing sheet 3a for covering a rear side of the pad body 2 and a facing sheet 3b for covering a front side of the pad body 2. The facing sheet 3b is laminated with a polyurethane film. The sheets 3a and 3b may be bonded to each other by specific adhesion techniques described hereinafter. The breast adjusting pad 1 which is the figure adjusting pad of the embodiment shown in FIG. 1 is provided on an outer periphery thereof with an edging fabric 5, SO that the pad body 2, facing sheet 3b and backing sheet 3a are bound-seamed together by the edging fabric 5.

Now, the figure adjusting pad of the illustrated embodiment will be described in more detail hereinafter.

The silicone gel layer 2b is basically made of an unfoamed silicone gel so as to exhibit an elasticity of a suitable level. A silicone gel suitable for use for the silicone gel layer 2b is an addition reaction type silicone polymer obtained by curing a mixture of diorganopolysiloxane (hereinafter referred to as "ingredient A") expressed by the following formula (1):

$$RR^1{}_2SiO\text{---}(R^2{}_2SiO)_n SiR^1{}_2R \qquad (1)$$

wherein R is an alkenyl group, $R^1$ is a monovalent hydrocarbon radical free of any aliphatic unsaturated bond, $R^2$ is a monovalent aliphatic hydrocarbon radical (a methyl group content in $R^2$ being at least 50 mol % and an alkenyl group content in $R^2$ being 10 mol % or less when it contains an alkenyl group), n is a value sufficient to permit the ingredient A to have viscosity of 100 to 100,000 cSt at a temperature of 25° C., and organohydrogenpolysiloxane (hereinafter referred to as "ingredient B") which has viscosity of 5000 cSt or less at a temperature of 25° C. and hydrogen atoms bonded directly to at least two Si atoms in one molecule thereof, which mixture is so adjusted that a ratio (molar ratio) of the sum total of alkenyl groups contained in the ingredient A to the sum total of hydrogen atoms bonded directly to Si atoms in the ingredient B is 0.1 to 2.0.

Now, the silicone gel will be more detailedly described hereinafter.

The ingredient A is a compound having a straight-chain molecular structure wherein alkenyl groups R at both ends of the molecule add to hydrogen atoms bonded directly to Si atoms in the ingredient B to form a crosslinking structure. The alkenyl groups present at both terminals of the molecule are each preferably a lower alkenyl group. The alkenyl group is particularly preferably a vinyl group in view of reactivity.

Also, $R^1$ present at each of the terminals of the molecule is a monovalent hydrocarbon radical free of any aliphatic unsaturated bond and includes, for example, an alkyl group such as a methyl group, a propyl group, a hexyl group or the like; a phenyl group; and a fluoroalkyl group.

In the formula (1) described above, $R^2$ is a monovalent aliphatic hydrocarbon radical and includes, for example, an alkyl group such as a methyl group, a propyl group, a hexyl group or the like and a lower alkenyl group such as a vinyl group or the like. Also $R^2$ contains at least 50 mol % of methyl group. When $R^2$ contains an alkenyl group, the content is preferably 10 mol % or less. The presence of alkenyl in an amount more than 10 mol % in $R^2$ causes crosslinking density of the ingredient to be excessively high, resulting in the viscosity being excessively increased. n is set to be a value sufficient to permit the ingredient A to apossess viscosity of 100 to 100,000 cSt at a temperature of 25° C. and preferably within the range of from 200 to 20,000 cSt.

The ingredient B is a crosslinking agent for the ingredient A, wherein the hydrogen atoms bonded directly to the Si atoms add to alkenyl groups in the ingredient A to cure the ingredient A. Various kinds of materials having molecular structures such as a straight-chain structure, a branched-chain structure, a cyclic structure, a net structure and the like may be used for the ingredient B, so long as they exhibit the above-described function of the ingredient B.

To the Si atoms in the ingredient B are bonded organic groups in addition to the hydrogen atoms. The organic groups each are normally a lower alkyl group such as a methyl group. And viscosity of the ingredient B at 2° C. is set to be normally 5000 cSt or less and preferably 500 cSt or less. The ingredient B of such a structure includes organohydrogenpolysiloxane of which both terminals each are blocked with a triorganosiloxane group, a copolymer of diorganosiloxane and organohydrogensiloxane, tetraorganotetrahydrogensiloxane, a copolymer siloxane of ½ unit of $HR^1{}_2SiO$ and ½ units of SiO, and a copolymer polysiloxane of ½ unit of $HR^1{}_2SiO$, ½ unit of $R^1{}_3SiO$ and ½ units of SiO. $R^1$ is the same as described above with respect to the formula (1).

Subsequently, the ingredients A and B are mixed together so that a ratio of the total molar amount of alkenyl groups in the ingredient A to the total molar amount of hydrogen atoms bonded directly to the Si atoms in the ingredient B is normally between 0.1 and 2.0 and preferably between 0.1 and 1.0, and then subjected to a curing reaction.

The curing reaction normally takes place using a catalyst. The catalyst suitable for use for this purpose is a platinum catalyst. The platinum catalyst includes, for example, finely ground elemental platinum, chloroplatinic acid, platinum oxide, a complex salt of platinum and olefin, and a complex of platinum alcoholate, chloroplatinic acid and vinylsiloxane. Such complex salts each are used in an amount of 0.1 ppm or more (in platinum equivalent) and preferably 0.5 ppm or more based on the sum total weight of the ingredients A and B. The upper limit of amount of the catalyst used is not specified; however, when it can be used in the form of liquid or solution, a sufficient amount is 200 ppm or less.

The ingredients A and B are mixed with the catalyst to prepare a mixture and the resultant mixture is then left to stand at a room temperature or heated, resulting in being cured, so that the silicone gel described above is prepared. Measurement according to Japanese Industrial Standard (JIS) K-2207-1980 (load: 50 g) indicates that the silicone gel thus obtained normally exhibits penetration of 5 250 and that according to JIS-K2220 indicates that it exhibits a consistency of 5 to 200. Hardness of the silicone gel is varied depending on the crosslinking structure formed between the ingredient A and the ingredient B.

Viscosity of the silicone gel before curing and its penetration after curing may be adjusted by previously adding silicone oil having methyl groups at both terminals thereof to the silicone gel obtained in an amount of 5 to 75% by weight. The silicone gel is thus adjusted. Alternatively, a commercially available silicone gel may be used to this end.

The silicone gel may include, in addition to the above-described ingredients A and B and catalyst, an agent providing thixotropic properties, a pigment, a cure retarder, a flame retarder and a filler, as well as a finely powdered deodorizer mainly consisting of oxide, water-absorbent resin and the like so long as they do not deteriorate characteristics of the silicone gel. Also, microballoons may be incorporated as a filler in the silicone gel. For this purpose, fillers manufactured under "Fillite" (registered trademark) by Nippon Fillite Kabushiki Kaisha and those sold under "EXPANCEL" (registered trademark) by the same company may be commercially available.

The foamed layer 2a laminated on the silicone gel layer 2b thus formed is required to exhibit satisfactory air-permeability. For example, a silicone foam having magnification of foaming within a range of from 10 to 15 and specific gravity of 0.1 or less and particularly adjusted so as to permit the silicone gel of the above-described composition and properties to be foamed during curing may be conveniently used for this purpose. The silicone foam may be commercially available under tradenames or products codes "Tosfoam XE18-A9923", "X-31-878-5" and "X-1075", and "SEF 10" from Toshiba Silicone Kabushiki Kaisha, Shin-Etsu Kagaku Kogyo Kabushiki Kaisha and Toray Dow Corning Silicone Kabushiki Kaisha, respectively.

A silicone foam inherently forms closed cells. Thus, in the illustrated embodiment, the silicone foam is pressed or somewhat crumpled to break cell walls, resulting in interconnected cells being formed. Alternatively, the foamed layer 2a may be formed of a pseudo-foamed gel made by elution techniques wherein, for example, sodium chloride is added in the form of a foaming medium to the above-described silicone gel, followed by curing and then the silicone gel is subjected to salt removal or desalting, resulting in cells being formed by traces of elution of the salt. On the other hand, the foamed layer 2a may be formed of a foam of a millable-type silicone rubber obtained by subjecting high-molecular straight-chain or branched polyorganosiloxane to crosslinking by means of a vulcanizing agent. The siloxane may have a phenyl group, a fluoro group or the like incorporated therein, to thereby provide a silicone raw rubber. Such incorporation permits the siloxane to be provided with various properties. Alternatively, the foamed layer 2a may be formed of a foam such as an urethane foam or the like.

Now, the cover sheet 3 for covering the pad body 2 constituted by the silicone gel layer 2b and foamed layer 2a will be described hereinafter. In the illustrated embodiment, the cover sheet 3, as described above, is basically constructed by the backing sheet 3a for covering the rear side of the pad body 2 and the facing sheet 3b for covering the front side of the pad body 2, by way of example. The backing sheet 3a is required to exhibit satisfactory air-permeability and the facing sheet 3b is required to exhibit satisfactory stretchability. The backing sheet 3a is formed by thermally bonding a non-woven fabric or a knitted web S of increased air-permeability to the foamed layer 2a by an air-permeable hot melt 23 described hereinafter. The facing sheet 3b includes a knitted web S of increased stretchability arranged on an outer side thereof and a polyurethane film P arranged on an inner side thereof and laminated on the knitted web S.

The knitted web S is preferably a stretchable and air-permeable knitted web selected from a tricot, a raschel, a grey sheeting (plain stitch), a circular rib fabric (rib stitch), a smooth (interlock stitch) and the like. A tricot is particularly preferable because it is readily available. The knitted web S may be made of a material conventionally used for a fabric. The material includes, for example, a natural fiber such as cotton, silk or the like and a chemical fiber such as nylon, polyester, or the like. When the material is formed into a fabric, it preferably has a chemical fiber of thermoplasticity incorporated therein. The fabric may be raised. The term "rear surface" or "rear side" used herein in connection with the knitted web S means a surface or side thereof contacted with the pad body 2 or polyurethane film P and the term "front surface" or "front side" means a surface or side thereof opposite to the "rear surface" or "rear side".

Figure 10A:
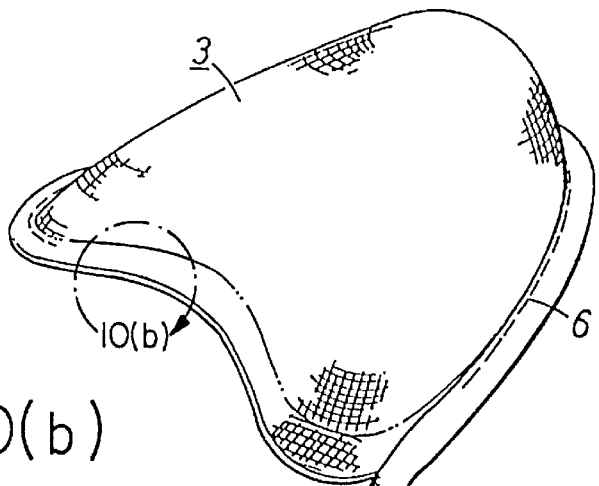
FIG. 10 is a perspective view showing a sewing step in a process of the present invention.
Figure 10B:
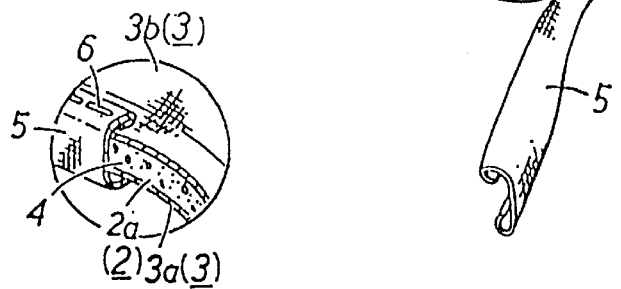
Figure 11:
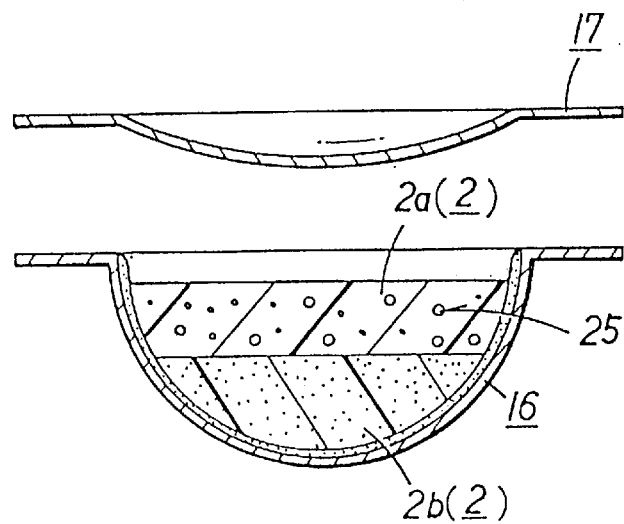
FIG. 11 is a vertical sectional side elevation view showing formation of a rear surface or side of a pad body by means of a mountain forming mold.

The non-woven fabric described above may be either a paper-type or a web-type. The web-type non-woven fabric is particularly suitable for use for this purpose, because it is readily cut, light-weight and substantially free of fraying. Also, a combination of the polyurethane film P with the silicone gel layer 2b is required to exhibit flexibility and elasticity close to the skin. In the illustrated embodiment, a soft polyurethane film which has a thickness as small as about 100 $\mu$m and of which hardness defined by JIS-K6301 is within a range between 65° and 85° may be used by way of example. Further, the breast adjusting pad 1, which is the figure adjusting pad of the illustrated embodiment, is provided at a periphery thereof with, a lug 4. For the lug 4, as shown in FIGS. 1 and 10, the pad body 2 in the form of a thin layer is arranged between the facing sheet 3b and the backing sheet 3a. In FIGS. 1 and 10, the pad body 2 is represented by the foamed layer 2a. The lug 4 is subjected to such bound-seaming as described above.

More particularly, the edging fabric 5, which has air-permeability substantially equal to the knitted web S, is applied to the lug 4 thus formed at the periphery of the figure adjusting pad 1 so as to cover the pad from the outside, and then the edging fabric 5 and lug 4 are subjected to bound-seaming by means of a yarn or thread 6. Also, the lug 4 is provided in a manner to be projected with a uniform thickness of several mm from the periphery of the pad body 2 and formed into a desired configuration. Alternatively, when the figure adjusting pad is cut at the possible limit of the above-described desired configuration, a periphery of the figure adjusting pad at which the cutting is carried out constitutes the lug 4. In the latter case, any margin is not substantially provided at the periphery of the figure adjusting pad, so that the bound-seaming takes place at a portion of the pad body 2 positioned by a distance of 2 to 3 mm inwardly of the periphery. This causes a portion of the pad body 2 forming the lug 4 to be compressed, so that the lug 4 is hardened as if a core is incorporated therein, resulting in the periphery of the figure adjusting pad 1 exhibiting increased shape retention.

Now, a process for manufacturing a figure adjusting pad according to the present invention will be described hereinafter in connection with the breast adjusting pad 1 with reference to FIGS. 1 to 13.

Figure 2:
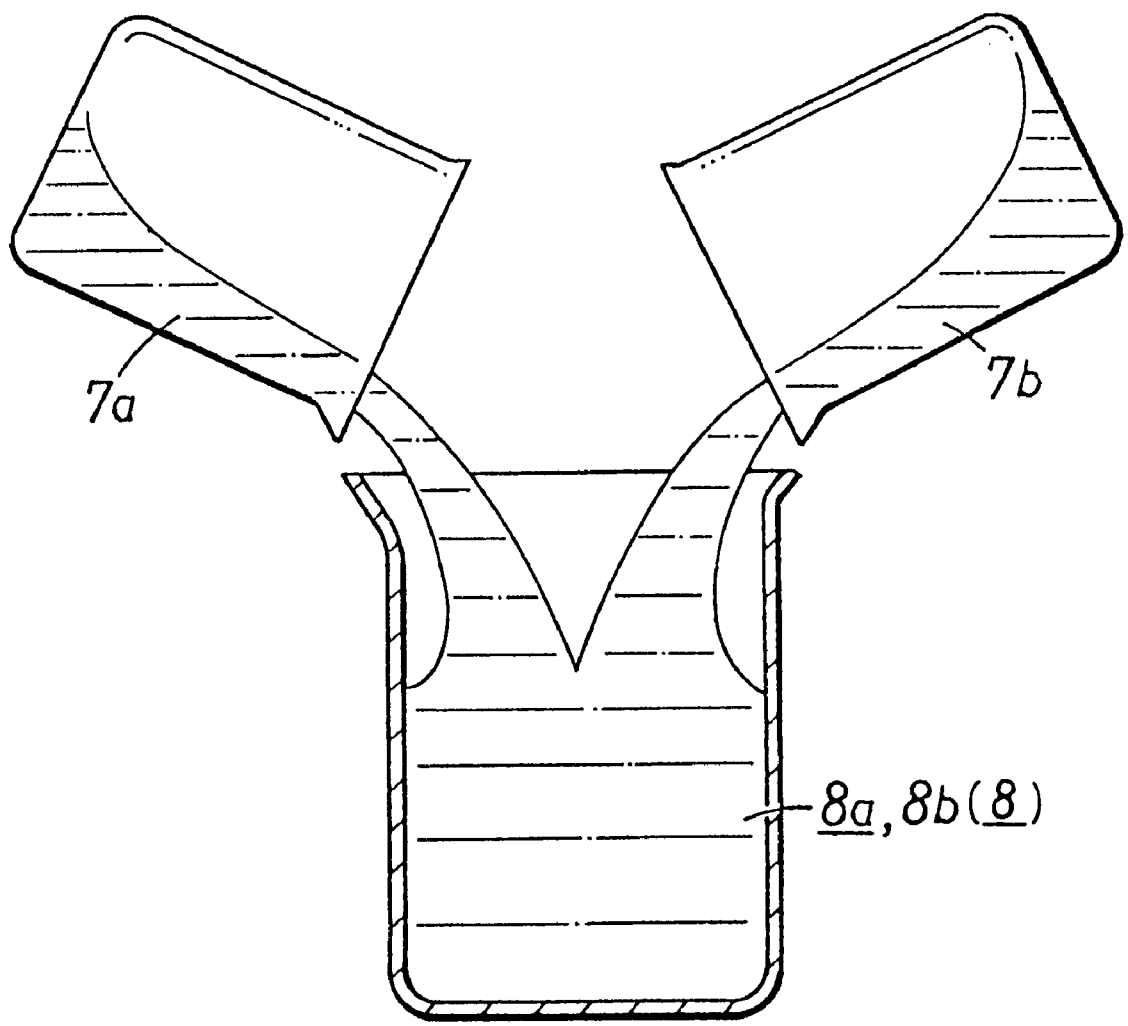
FIG. 2 is a schematic view showing preparation of a stock solution used in a process for preparing a figure adjusting pad according to the present invention.

First, as shown in FIG. 2, a stock solution 8 is prepared for manufacturing the figure adjusting pad 1. In the illustrated embodiment, a silicone gel is used. In FIG. 2, reference character 7a designate a silicone gel agent A and 7b is a silicone gel agent B. Suitable materials such as a catalyst, a pigment and the like may be added thereto as required. In FIG. 2, reference character 8a designates a stock solution for the foamed layer 2a. In the illustrated embodiment, a two-pack system silicone foam of the addition reaction type wherein the agent A and agent B are mixed at a ratio of 1:1 so as to exhibit desired magnification of foaming may be used. Thus, a stock solution 8 is prepared.

(1) Shaping Sheet Adhering Step:

A shaping sheet adhering step adheres the knitted web S and polyurethane film P, which constitute the facing sheet 3b to a shaping sheet 11. In the illustrated embodiment, a thermoplastic copolyester film of 0.4 mm in thickness acting as the shaping sheet 11, a somewhat thick knitted web S such as a tricot knitted web or the like and a polyurethane film P of about 100 µm in thickness are used by way of example. The thermoplastic copolyester film 11 used in the illustrated embodiment is a transparent non-crystalline polymer obtained by substituting 1,4-cyclohexane dimethanol for a part of a glycol ingredient in polyethylene terephthalate resin. The polymer used had a glass transition point of about 80° C. (Tg) measured by DSC and an average molecular weight of about 26000 (Mn). For example, the thermoplastic copolyester film 11 satisfying such conditions may be commercially available under a tradename "PETG 6763" from Nagase Sangyo Kabushiki Kaisha. The above-described construction of the illustrated embodiment is for providing a protuberance forming mold 16. A construction for providing a recess forming mold 17 used for forming the rear side of the pad body 2 comprises only penetration engagement between the thermoplastic copolyester film 11 and the knitted web S.

Figure 3A:
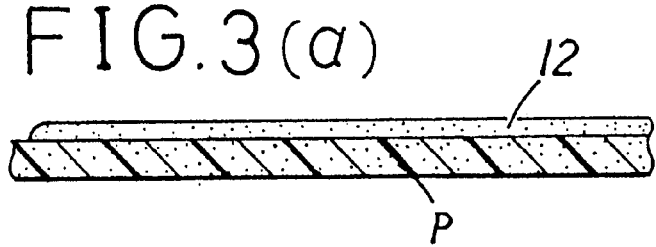
FIGS. 3(a) to 3(d) are vertical sectional side elevation views stepwise showing a shaping sheet adhering step in a process for manufacturing a figure adjusting pad according to the present invention.
Figure 3B:
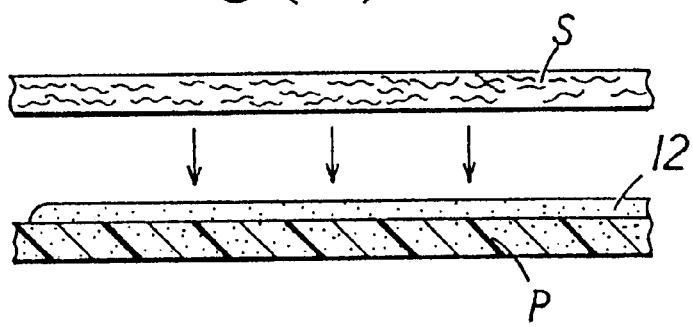
Figure 3C:
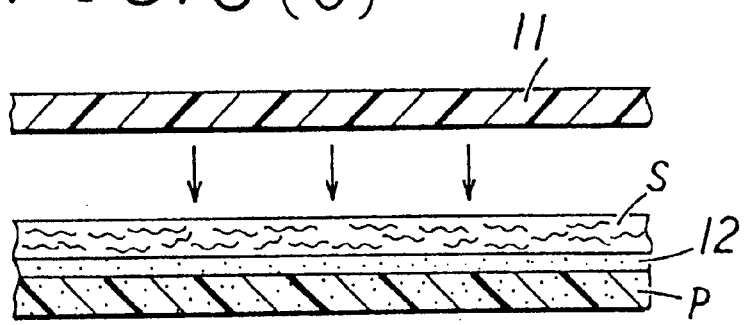
Figure 3D:
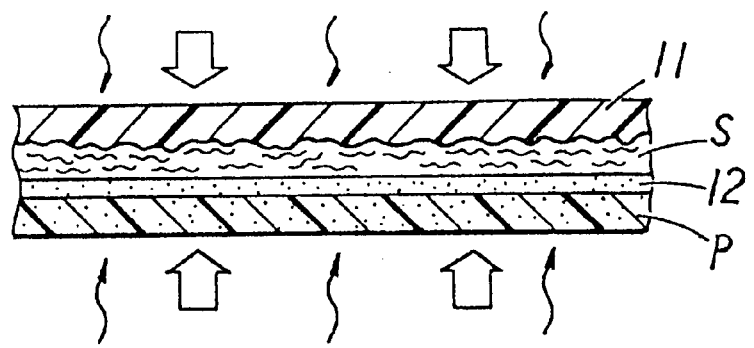
Figure 4A:
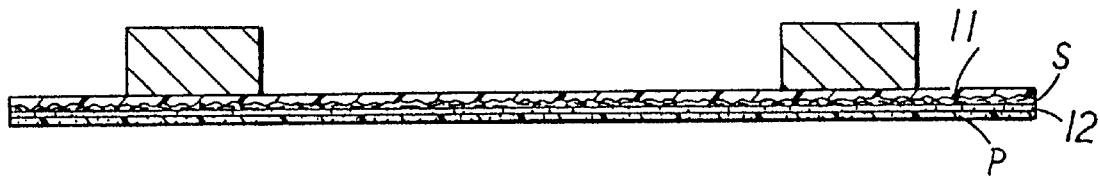
FIGS. 4(a) and 4(b) are vertical sectional side elevation views stepwise showing a protuberance forming mold forming step in a process of the present invention.
Figure 4A:
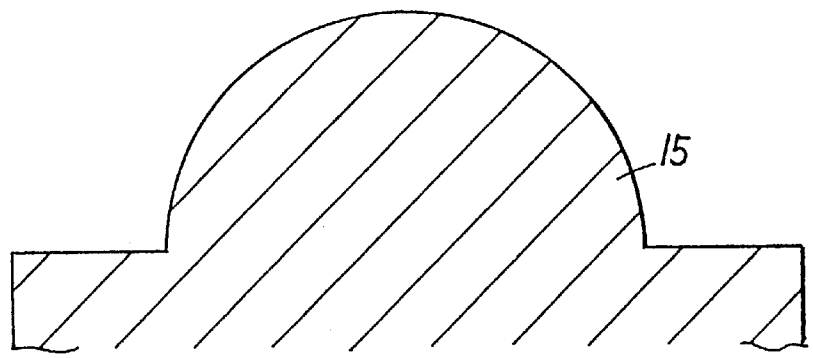
Figure 4B:
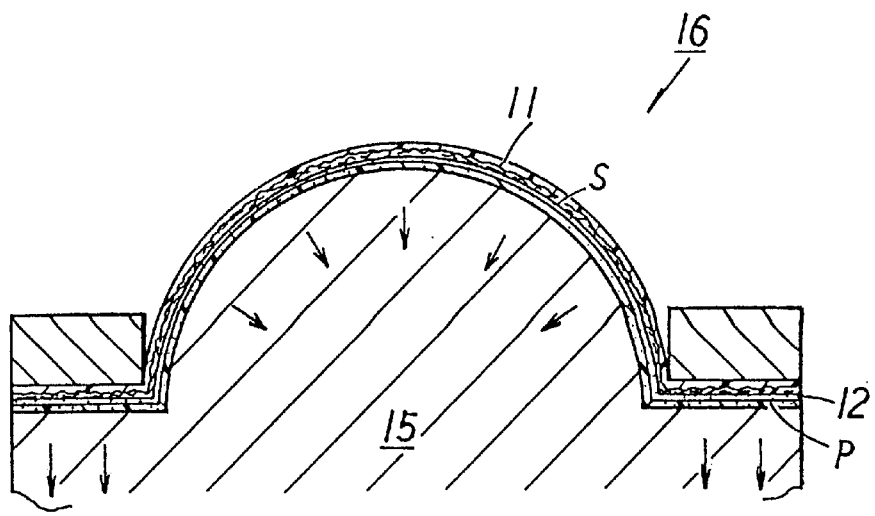

Now, adhesion of the above-described members to each other will be described in detail hereinafter. First, as shown in FIG. 3(a), a polyurethane adhesive 12 is applied to one surface of the polyurethane film P subjected to laminating. The term "laminating" used herein means "processing into a leaf-like shape". The polyurethane film P of a leaf-like shape tends to extend and be deformed or strained. Thus, a release paper (not shown) functioning as a base element for reinforcing the leaf-like polyurethane film P is laminated on the film P. Then, the knitted web S is arranged on the surface of the polyurethane film P to which the polyurethane adhesive 12 is applied, as shown in FIG. 3(b). Thereafter, as shown in FIG. 3(c), the thermoplastic copolyester film 11 is put on the knitted web P, followed by pressurizing and heating, resulting in a sheet-like member being provided as shown in FIG. 3(d). In the sheet-like member thus formed, the polyurethane film P and knitted web S are firmly adhered to each other through the polyurethane adhesive 12, whereas the knitted web S and thermoplastic polyester film 11 are kept temporarily adhered to each other by penetration engagement due to penetration of a part of the thermoplastic polyester film 11 into stitches of the knitted web S.

(2) Protuberance Forming Mold Forming Step:

A protuberance forming mold forming step forms the shaping sheet 11 having the facing sheet 3b adhered thereto into the protuberance forming mold 16 of a configuration corresponding to a desired configuration of the breast adjusting pad 1 while keeping the facing sheet 3b facing inside. The recess forming mold 17 used for forming the rear side of the pad body 2, as will be noted from the foregoing, is formed into a desired configuration by projecting the side of the shaping sheet 11 to which the backing sheet 3a is adhered.

The step is carried out using the thermoplastic polyester film 11, knitted web S and polyurethane film P which, are integrated with each other as described above. The release paper laminated on the polyurethane film P is peeled therefrom and then the protuberance forming mold 16 is formed by means of a vacuum mold forming machine or die 15. The protuberance forming mold 16, as disclosed in Japanese Patent Application Laid-Open Publication No. 131007/1993, may be formed on a whole periphery thereof with an overflow receiving groove for receiving an overflow of the stock solution 8 poured into the mold 16 and a peripheral overflow passage for guiding the overflow from the mold to the overflow receiving groove. However, in the illustrated embodiment, a silicone foam which requires 30 to 90 seconds for foaming and curing is used as the stock solution 8a for the foamed layer 2a. Therefore, an overflow receiving groove and peripheral overflow passage as described above are not necessarily required in the illustrated embodiment. A mold forming machine or die utilizing a compressed air pressure may be substituted for the vacuum forming machine 15. Alternatively, both machines may be used.

Figure 5C:
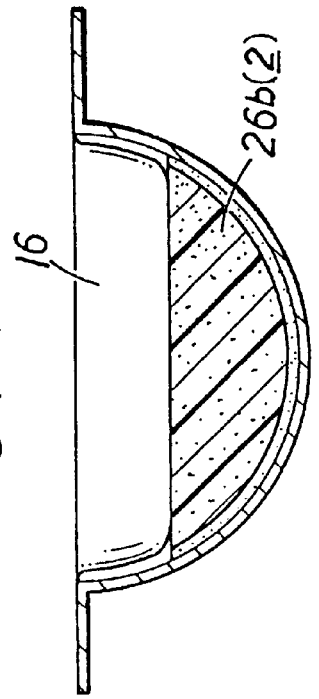
FIGS. 5(a) to 5(d) are vertical sectional side elevation views stepwise showing a first half of a pad body forming step in a process of the present invention.

(3) Pad Body Forming Step:

A pad body forming step pours the stock solution 8 into the protuberance forming mold 16 formed in the protuberance forming mold forming step described above and then cures it by heating, so that the pad body 2 comprising the foamed layer 2a and silicone gel layer 2b may be formed into a desired configuration. More particularly, as shown in FIG. 5(a), the polyurethane film P of the protuberance forming mold 16 is subject to a primer treatment and then left to stand for 30 minutes at a room temperature. Then, as shown in FIG. 5(b), the gel layer stock solution 8b is charged in an amount required for forming the silicone gel layer 2b into the protuberance forming mold 16 while being conformed to a configuration of the protuberance forming mold 16. The amount of stock solution 8b to be charged depends on the size of protuberance forming mold 16 and a ratio of the silicone gel layer 2b to the foamed layer 2a.

The stock solution 8b is heated in a curing furnace of a large capacity upon charging, followed by cooling, resulting in it being semi-cured or fully cured so as to be prevented from being mixed with the foamed layer stock solution 8a, which will then be poured into the mold. Thereafter, an additional primer is applied to a portion of the polyurethane film P into which the foamed layer stock solution 8a is to be charged, as shown in FIG. 5(c). Application of the additional primer enhances the primer effect as compared with common use of the above-described primer applied for forming the silicone gel layer 2b.

In the illustrated embodiment, the primer used for formation of the silicone gel layer 2b may comprise a mixture of "Primer X" and "Primer Y" which are commercially available from Toray Dow Corning Silicone Kabushiki Kaisha and the additional primer for the foamed layer 2a may comprise "Primer A" commercially available from Toray Dow Corning Silicone Kabushiki Kaisha.

Figure 5D:
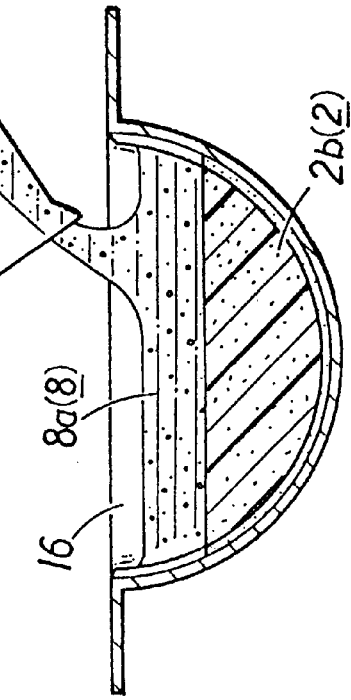
Figure 5A:
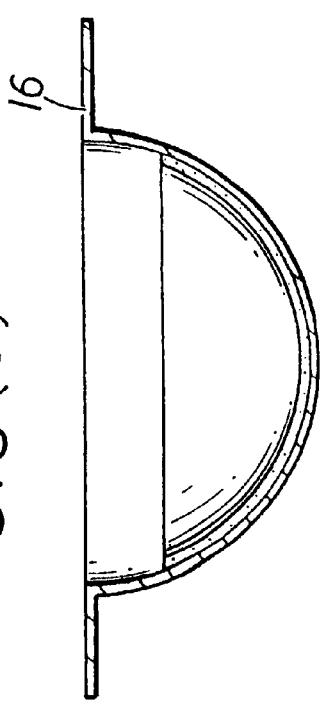
Figure 5B:
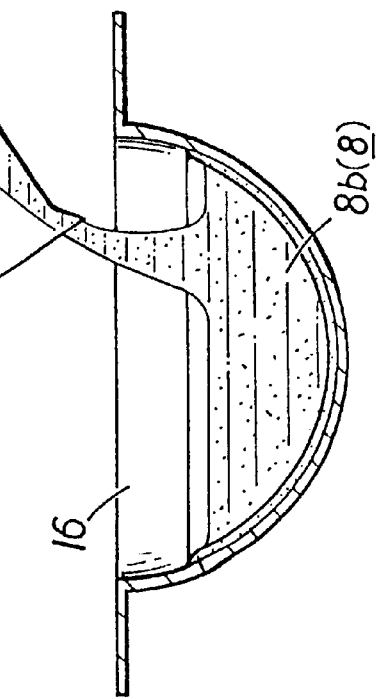
Figure 6A:
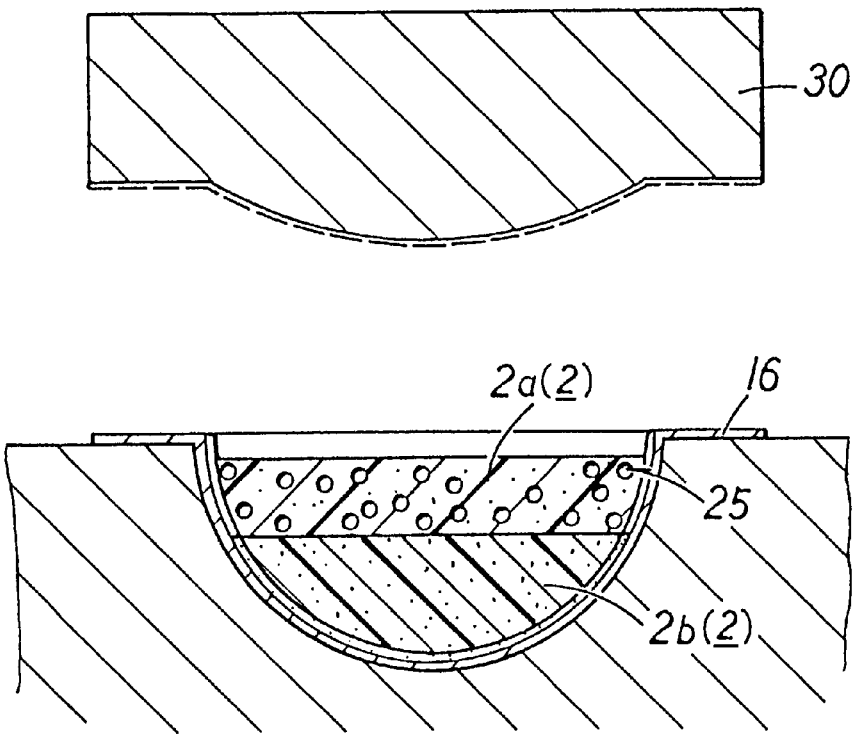
FIGS. 6(a) and 6(b) are vertical sectional side elevation views stepwise showing a second half of a pad body forming step in a process of the present invention.
Figure 6B:
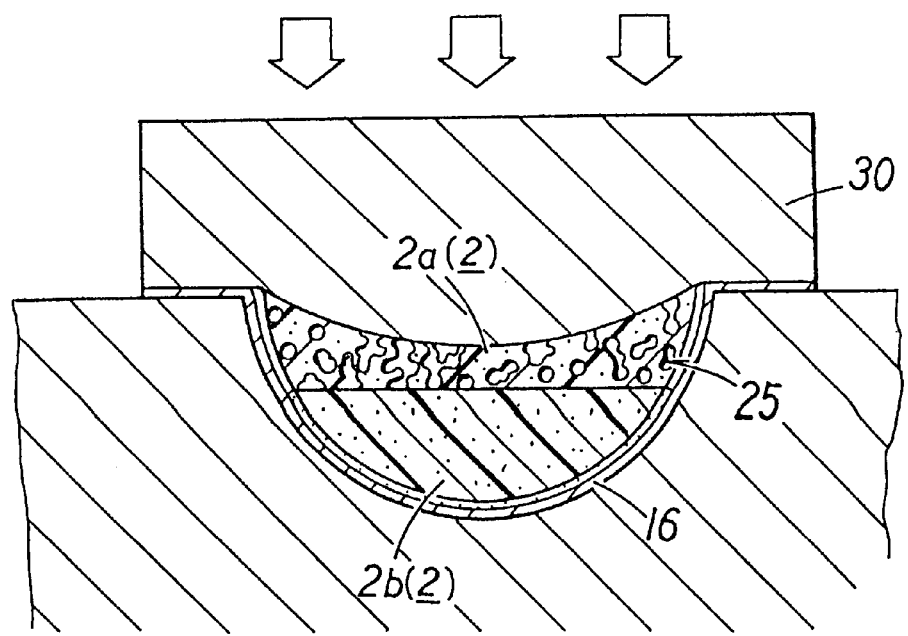

Then, the foamed layer stock solution 8a is downwardly poured toward the silicone gel layer 2b thus formed in the protuberance forming mold 16, as shown in FIG. 5(d). After the foamed layer stock solution 8a is cured to a certain degree, resulting in the foamed layer 2a being provided, the foamed layer 2a is downwardly pressed by means of a recess forming die 30 coated with Teflon, by way of example, as shown in FIGS. 6(a) and 6(b). The pressing causes a closed-cell structure of the foamed layer 2a to be changed into an open-cell structure, to thereby provide the foamed layer 2a with air-permeability. Also, this Causes the rear side of the pad body 2 to be formed into a desired recessed configuration by the recess forming die 30. Alternatively, the recess forming die 30 may be replaced with the recess forming mold 17 shown in FIG. 11. Formation of the foamed layer 2a into the above-described open-cell structure by pressing is confirmed by a breathing sound generated from the foamed layer 2a during the pressing. The sound indicates that the closed-cell structure of the silicone foam is at least partially changed into the open-cell structure.

Figure 7A:
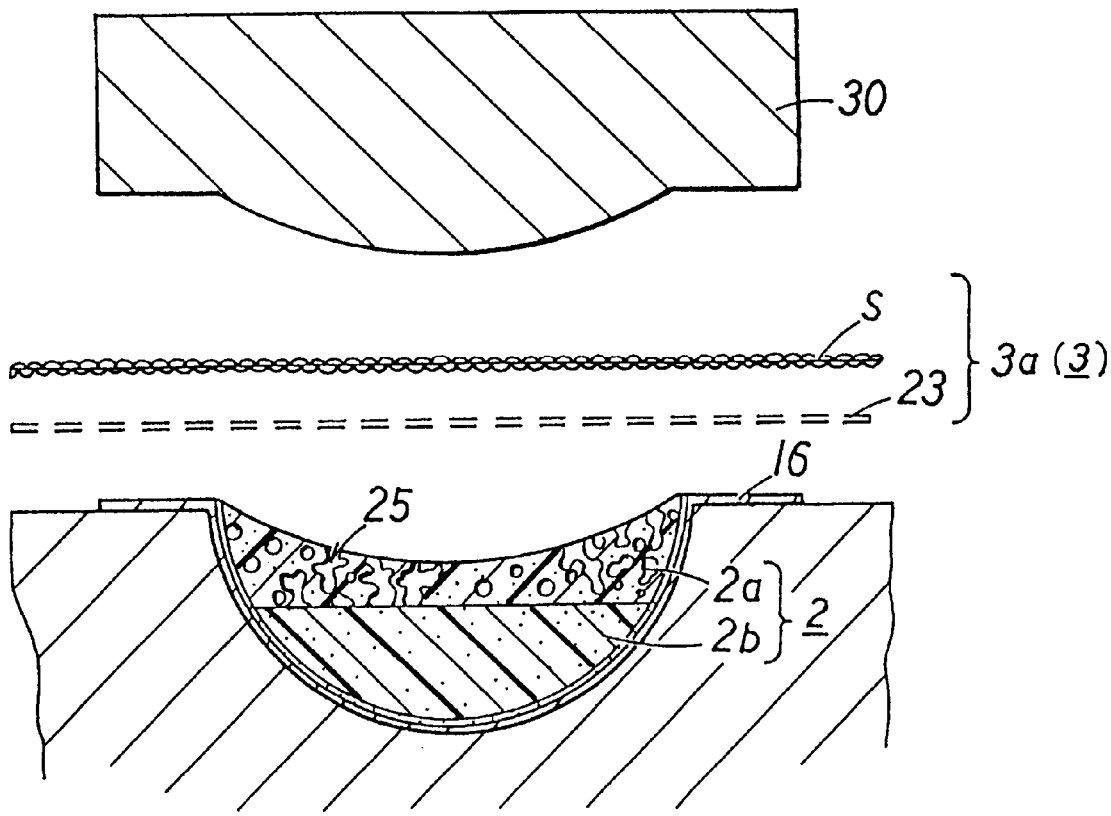
FIGS. 7(a) and 7(b) are vertical sectional views stepwise showing a backing sheet adhering step in a process of the present invention.
Figure 7B:
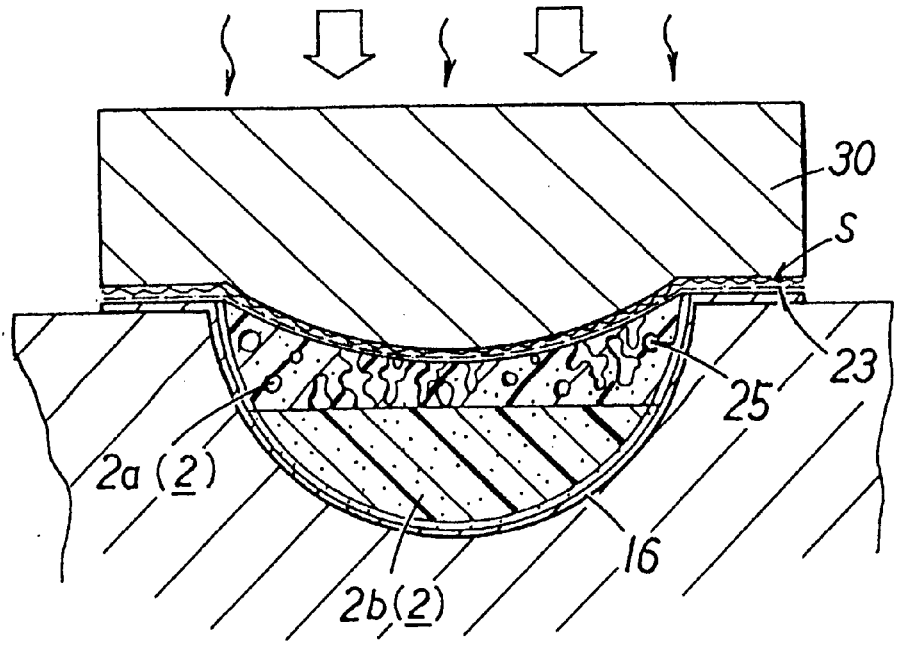
Figure 8:
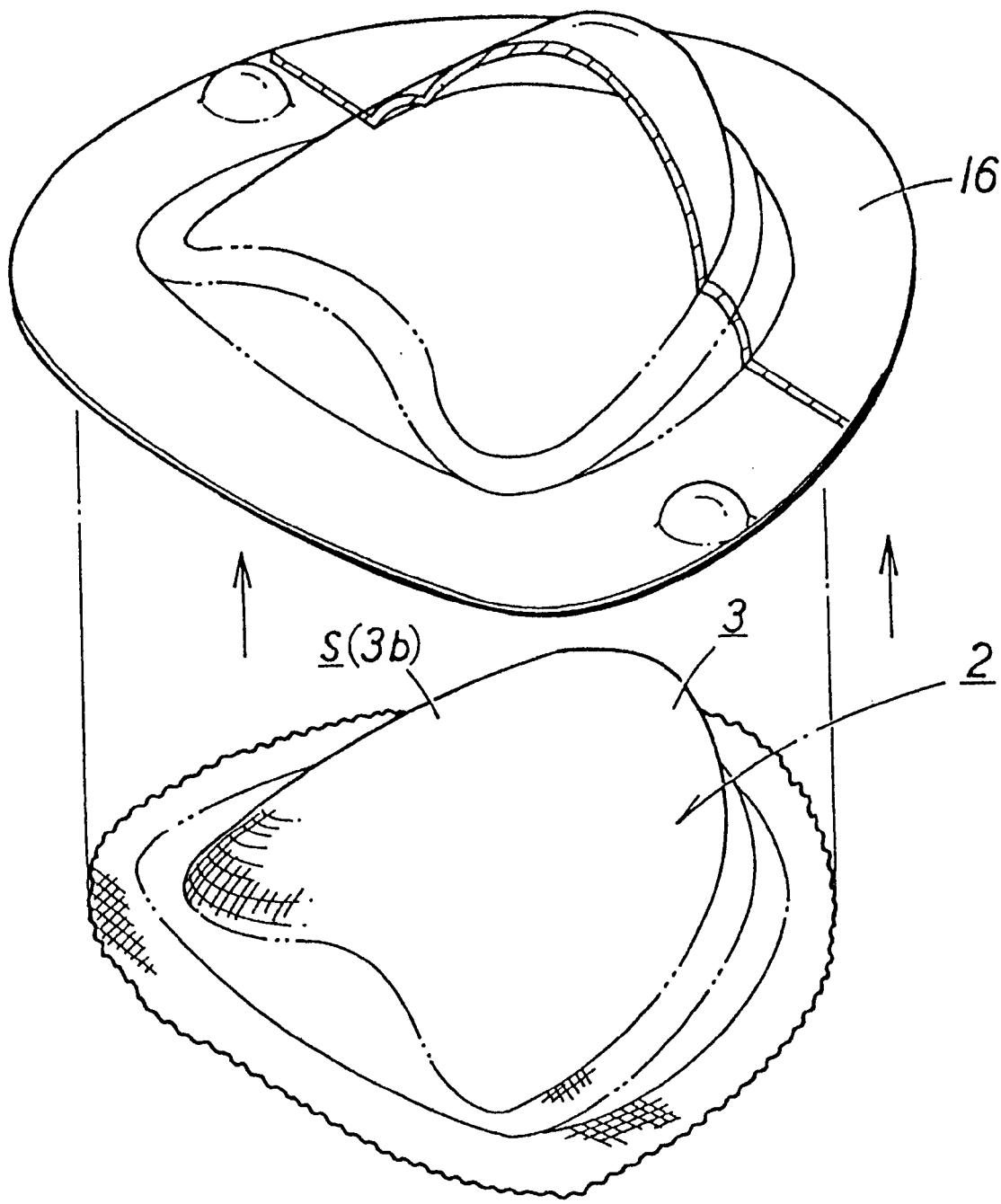
FIG. 8 is a perspective view showing release of a protuberance forming mold in a mold release step in a process of the present invention.

(4) Backing Sheet Adhering Step:

A backing sheet adhering step adheres the backing sheet 3a to the rear side of the pad body 2 thus formed in the above-described pad body forming step. In the backing sheet adhering step, as shown in FIGS. 7(a) and 7(b), air-permeable hot melt 23 is downwardly put on the rear side of the pad body in the protuberance forming mold 16 and more particularly on the recessed side of the foamed layer 2a of the pad body 2. Then the non-woven fabric or knitted web S increased in air-permeability is put on the hot melt 23. Then, the recess forming die 30 is used again to heat and pressurize the air-permeable hot melt 23 and knitted web S or non-woven fabric, to thereby adhere the backing sheet 3a to the recessed side of the foamed layer 2a without interposing any air-permeability deteriorating or interrupting layer therebetween. In the illustrated embodiment, the pressurizing may take place at a pressure of 130 g/cm$^2$ for 30 seconds. Also, the air-permeable hot melt 23 used may comprise a spidery hot melt of a sheet-like configuration formed with a plurality of air holes and have a METSUKE weight of about 10 to 100 g/m$^2$. For example, the hot melt 23 may have a METSUKE weight of 30 g/m$^2$. Also, the air-permeable hot melt 23 may be conveniently made of a material commercially available under "DYNAC" (registered trademark), which is manufactured by Kureha Tech Kabushiki Kaisha and sold by Toyo Boseki Kabushiki Kaisha. Pressurizing and heating of the air-permeable hot melt 23 and knitted web S or non-woven fabric may take place using a pressing die other than the recess forming die 30.

(5) Mold Release Step:

In a mold release step, the recess forming die 30 is upwardly retracted from the pad body 2 to which the backing sheet 3a is adhered and then the protuberance forming mold 16 is removed from the pad body 2 having the backing sheet 3a adhered thereto. At this time, no adhesive is interposed between the knitted web S arranged on the front side of the pad body 2 and the shaping sheet 11 constituted by the thermoplastic copolyester film, and both are under penetration engagement, wherein the shaping sheet is kept partially penetrated into the stitches of the knitted web S, so that the mold release step may be readily accomplished.

Figure 9A:
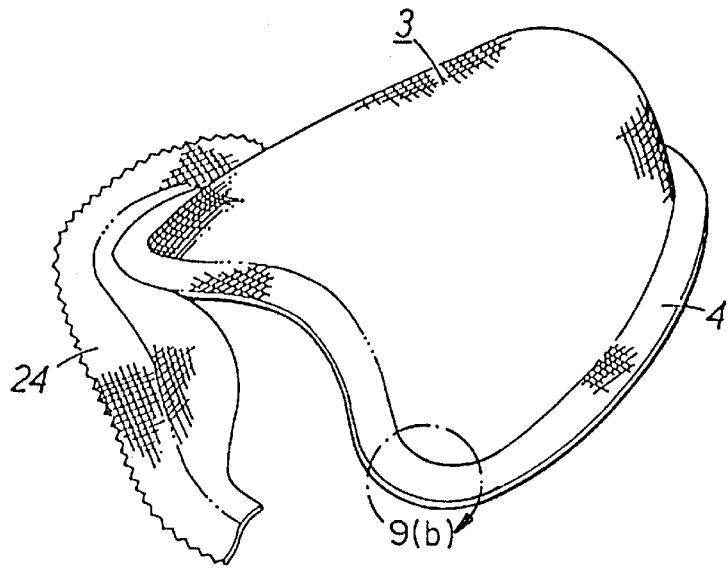
FIG. 9 is a perspective view showing a cutting step in a process of the present invention.
Figure 9B:
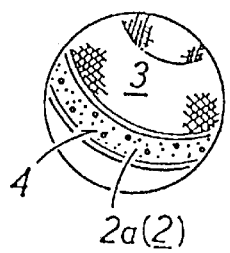

(6) Cutting Step:

The pad body 2 released from restriction by the protuberance forming mold 16 and recess forming die 30 has an unnecessary extra margin or extra peripheral portion 24 formed at an outer periphery thereof, as shown in FIG. 9. A cutting step cuts off the extra peripheral portion 24 from the pad body 2 to cause the foamed layer 2a to be exposed at the periphery of the pad body 2 covered with the cover sheet 3. The breast adjusting pad 1 of the illustrated embodiment, as described above, is cut at the possible limit of the above-described desired configuration, so that the periphery of the figure adjusting pad at which the cutting is carried out constitutes the lug 4. Thus, the breast adjusting pad 1 does not cause a user to have an unpleasant feeling toward the cut portion. The breast adjusting pad 1 thus subjected to the cutting treatment may have a fabric piece for indication attached thereto by sewing or the like. Any suitable indication, such as the name of a manufacturer, a product code or the like, may be displayed on the fabric piece.

(7) Sewing Step:

A sewing step subjects the lug 4 of the breast adjusting pad 1 thus obtained to bound-seaming to provide a final product. More particularly, as shown in FIG. 10, the edging fabric 5 is applied from outside to the lug 4 of the breast adjusting pad 1 so as to surround it. Then, the pad body 2 (foamed layer 2a) formed into a configuration like a thin layer and the facing and backing sheets 3b and 3a are sewed together by means of the thread 6, to thereby form the edging fabric 5 into a baglike shape. In the illustrated embodiment, the bound-seaming may be conveniently carried out at a portion of the pad body 2 positioned by a distance of 2 to 3 mm inwardly of an outer end of the pad body 2. The bound-seaming takes place over the whole periphery of the lug 4, so that a portion of the pad body 2 in the lug 4 may be compressed, resulting in it being hardened, to thereby act as a core of the lug. Thus, the lug 4 is shaped, so that the final product or breast adjusting pad 1 may be obtained.

Bound-seaming is a technique of double-sewing an end of a fabric and another fabric or tape while wrapping the former with the latter and is known as the best way of treating an end of a fabric. Thus, bound-seaming has been conventionally used for treating an end of high-quality fabric goods. Also, it has been used for providing fabric goods with strength. Further, the bound-seaming accomplishes sewing with any desired width or in any desired manner depending on a configuration of a fitment generally called "wrapper". In addition, it may be practiced twice or made when an object is complicated in structure or configuration.

The "shaping" of the lug 4 indicates that the bound-seaming permits a core to be formed in the lug to effectively establish a whole configuration of the breast adjusting pad, resulting in the pad exhibiting satisfactory shape retention. Also, a portion of the pad body 2 in the edging fabric 5 which is positioned by a distance of 2 to 3 mm outwardly of the thread 6 is permitted to expand due to its restoring force, to thereby cause the edging fabric 5 to expand. Thus, the breast adjusting pad 1 of the illustrated embodiment is favorably accepted as a part of lingerie and contributes to figure adjusting. After the sewing, the breast adjusting pad 1 may be coated with a body powder to remove surface tackiness from the pad 1. The body powder may mainly consist of mica.

In the embodiment described above, the closed-cell structure of the foamed layer 2a is converted into the open-cell structure by pressing using the recess forming die 30. Alternatively, it may be carried out by crumpling. In this instance, it is not required to carry out conversion of the closed-cell structure into the open-cell structure to a degree of 100%. It is merely required to provide the pad body 2 with desired air-permeability. Thus, conversion into the open-cell structure required may be accomplished by further pressing or crumpling the pad body 2 after the mold release step or laundering it after the sewing step.

Also, when the silicone foam is used as a material for the foamed layer 2a as described above, the closed-cell structure of the foamed layer 2a is converted into the open-cell structure. Alternatively, the foamed layer 2a is formed of a foaming medium into a porous structure as described hereinafter, the foamed layer 2 may be subjected to a foaming treatment concurrently with or subsequent to the pressuring and heating treatment. More particularly, the foaming medium is added to the foamed layer stock solution 8a, to thereby form the foamed layer 2a cured to a certain degree, followed by placing of the foamed layer 2a in a suitable solvent to react the foaming medium with the solvent. This causes the foaming medium to be eluted from the foamed layer to provide voids 25.

Now, the foaming medium will be further described hereinafter. When the solvent is water, the foaming medium soluble in water may be formed of sodium polyacrylate, polyvinyl alcohol, methyl cellulose, carboxy methyl cellulose, polyethylene oxide, polyvinyl pyrrolidone, acrylic amide, glue, gelatin, casein, polypeptide, funori (glue plant), agar, sodium alginate, sodium chloride, dextrose and glucose, saccharose, natural polysaccharide such as prulan, xanthane gum or starch, sodium ascorbate, or the like. When acetone ethanol, methanol or the like can be used as the solvent in view of a material for a mold or the like, the foaming medium may be made of polyvinyl alcohol, methyl cellulose, ethyl cellulose, water-soluble nylon, shellac, styrol or the like.

Mere preparation of a porous silicone gel may be carried out according to the following and like techniques. Extinguishing techniques have a material extinguished by heating incorporated into a silicone gel stock solution to prepare a mixture, which is then cured by heating, and then the material is extinguished by heating to form voids 25. Shrinking techniques by drying has a swelled material incorporated in a silicone gel stock solution shrunk by drying and then separated. Microwave heating techniques have a volatile liquid of a large dielectric loss coefficient dispersed in a silicone gel stock solution and then subjected to dielectric heating in an electric field of a high frequency, resulting in an increase in temperature and thus expansion by vaporization. The silicone gel stock solution is cured by crosslinking; or the like. The foamed layer 2a and silicone gel layer semi-cured as described above are then pressurized and heated, resulting in being fully cured.

Figure 12A:
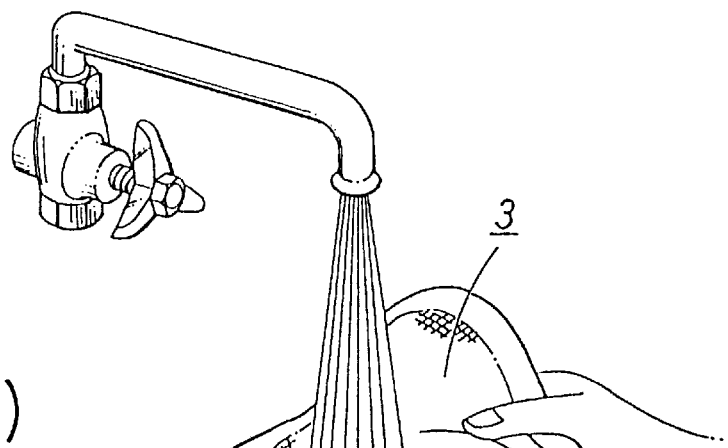
FIG. 12 is a perspective view showing salt removal or desalting carried out when salt is used as a foaming medium.
Figure 12B:
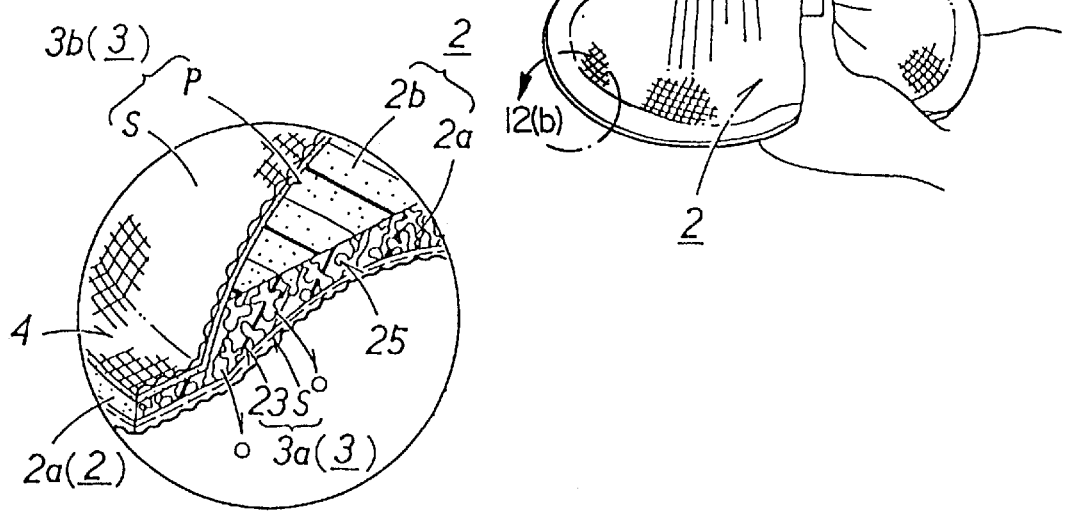

Now, use of a salt as the foaming medium will be briefly described hereinafter. After the foamed layer stock solution 8a containing a salt is cured to a certain degree and particles of the salt dispersed in the foamed layer 2a are positionally fixed, the foamed layer 2a formed is crumpled to render spaces occupied by the particles of the salt adjacent each other contiguous to each other, to thereby facilitate elution of the salt from the foamed layer 2a, as shown in FIG. 12, which shows the figure adjusting pad after the mold release step and before the cutting step. Then, the figure adjusting pad is dipped in water to dissolve the salt in the water. In this instance, a washing machine may be used or the figure adjusting pad is manually washed while being tenderly crumpled, to thereby cause the salt to be substantially removed from the pad. Then, finishing salt-removal or desalting is carried out, wherein a jet of water is applied to the pad body 2 through the cover sheet 3, to thereby fully remove the salt from the foamed layer 2a. Finally, the pad is dried in a blast dry oven, to thereby render the foamed layer 2a porous. The figure adjusting pad thus obtained is increased in air-permeability and decreased in weight.

The pad body forming step and backing sheet adhering step are not limited to the foregoing. The steps may be otherwise carried out according to such a procedure as disclosed in Japanese Patent Application No. 152796/1994.

The illustrated embodiment has been described in connection with the breast adjusting pad. However, the figure adjusting pad of the present invention is not limited to such a breast adjusting pad. For example, it may be conveniently applicable to a pad for a brassiere for plumping the breasts, a shoulder pad, a knee pad, a waist pad and the like.

As can be seen from the foregoing, the figure adjusting pad of the present invention comprises the pad body including the foamed layer increased in air-permeability and arranged on the wrong side thereof and the silicone gel layer arranged on the right side thereof, which are laminated on each other. The pad also Comprises the cover sheet for covering the outer surface of the pad body. The cover sheet includes the facing sheet for covering the front side of the pad body and the backing sheet for covering the rear side of the pad body. The facing sheet includes the knitted web increased in stretchability arranged on the front side thereof and the polyurethane film arranged on the rear side thereof and laminated on the knitted web. The backing sheet includes the non-woven fabric or knitted web increased in air-permeability which is thermally bonded to the foamed layer by means of the air-permeable hot melt. Such construction permits the figure adjusting pad to exhibit fat sensation close to the skin due to flexibility and elasticity of the silicone gel layer and weight sensation due to the silicone gel layer. Also, it permits the pad to be decreased in weight due to the foamed layer. Thus, the pad of the present invention can be formed into a desired weight. Also, the air-permeable hot melt improves air-permeability of the pad and the polyurethane film P provides the pad with suitable flexibility.

In the present invention, the silicone gel layer may be formed of a silicone gel of which consistency defined by JIS-K2220 is within a range between 75 and 105. This permits the pad of the present invention to exhibit flexibility and elasticity close to the skin.

In the present invention, the polyurethane film may be formed of flexible polyurethane of which hardness defined by JIS-K6301 is within a range between 65° and 85°. This, in combination with the silicone gel layer, permits the pad to exhibit optimum flexibility and elasticity.

In the present invention, the foamed layer may be formed into an open-cell structure by pressing or crumpling a silicone foam of 10 to 15 in magnification of foaming and 0.1 or less in gravity. This permits the pad to be substantially improved in air-permeability and decreased in weight.

In the present invention, the air-permeable hot melt may comprise the spidery sheet-like member provided with a plurality of air holes and has a METSUKE weight set to be 10 to 100 g/m$^2$. This ensures sufficient adhesion strength between the backing sheet and the foamed layer and improves air-permeability of the pad.

In the present invention, the knitted web may be formed by subjecting at least one of a natural fiber and a chemical fiber to tricot stitch, raschel stitch, plain stitch, rib stitch or interlock stitch. This provides the pad with increased stretchability, as well as satisfactory air-permeability and sweat absorption.

In the present invention, the silicone gel layer may be formed of a silicone gel having a material decreased in specific gravity added thereto. This permits the pad to be further decreased in weight.

In the present invention, the figure adjusting pad may further comprises the air-permeable edging fabric arranged on the periphery of the figure adjusting pad. The pad body, facing sheet and backing sheet are bound-seamed together by the edging fabric. This provides the pad with air-permeability of a desired level and increased shape retention.

Also, in the process of the present invention, the pad body forming step is carried out by pouring the gel layer stock solution into the protuberance forming mold formed in the protuberance forming mold forming step, pouring the foamed layer stock solution onto the gel layer stock solution to form the front side of the pad body and downwardly pressing the foamed layer being cured to concurrently carry out formation of the rear side of the pad body and formation of the open-cell structure of the foamed layer. Such construction significantly decreases a mold manufacturing cost and the number of steps of the process.

In the process of the present invention, the shaping sheet adhering step is carried out by adhering the polyurethane film to one surface of the knitted web increased in stretchability by means of the polyurethane adhesive, laminating the shaping sheet made of the thermoplastic copolyester film on the other surface of the knitted web to provide the laminate, and pressurizing and heating the laminate to form penetration engagement between the shaping sheet and the knitted web wherein the shaping sheet is partially penetrated into stitches of the knitted web, resulting in adhering the shaping sheet and knitted web to each other. This ensures firm joining between the polyurethane film and the knitted web and prevents deterioration in properties of the polyurethane film. Also, it prevents fat sensation of the pad body from being adversely affected.

In the process of the present invention, the backing sheet adhering step may be carried out by putting the air-permeable hot melt on the rear side of the pad body formed and arranged in the protuberance forming mold and putting the non-woven fabric or knitted web increased in air-permeability on the hot melt, followed by pressurizing and heating, leading to adhesion of the backing sheet. This permits an air passage to be formed in the figure adjusting pad, to thereby significantly improve air-permeability of the pad.

In the present invention, the pad body forming step.may be so carried out that the polyurethane film arranged in the protuberance forming mold is subjected to primer treatment before pouring of the gel layer stock solution and foamed layer stock solution. This ensures positive joining between two members different in material and eliminates use of any adhesive.

In the present invention, formation of the rear side of the pad body in the pad body forming step may take place by using the recess forming die or recess forming mold, carrying out pouring of the foamed layer stock solution, putting the recess forming die or recess forming mold on the foamed layer stock solution and pressing the foamed layer stock solution by means of the recess forming die or recess foaming mold. This permits the rear side of the pad body to be formed into a desired configuration and contributes a decrease in manufacturing cost of the mold.

While preferred embodiments of the invention have been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A figure adjusting pad comprising:
   a pad body having a front side, a rear side and an outer surface, said pad body comprising an air-permeable foamed layer and a silicone gel layer laminated with each other such that said air-permeable foamed layer is located at said rear side of said pad body and said silicone gel layer is located at said front side of said pad body with respect to each other; and
   a cover sheet covering said outer surface of said pad body, said cover sheet comprising a facing sheet covering said front side of said pad body and a backing sheet covering said rear side of said pad body;
   wherein said facing sheet has a facing sheet front side and a facing sheet rear side and comprises a stretchable knitted web on said facing sheet front side and a polyurethane film laminated on said knitted web on said facing sheet rear side; and
   wherein said backing sheet comprises an air-permeable material selected from the group consisting of a non-woven fabric and a knitted web, said air-permeable material being thermally bonded to said foamed layer by an air-permeable hot melt.

2. The figure adjusting pad of claim 1, wherein said silicone gel layer comprises a silicone gel having a consistency within a range between 75 and 105 as defined by JIS-K2220.

3. The figure adjusting pad as defined in claim 2, wherein said polyurethane film is formed of flexible polyurethane having a hardness within a range between 65° and 85° as defined by JIS-K6301.

4. The figure adjusting pad as defined in claim 2, wherein said foamed layer comprises an open-cell structure formed by pressing or crumpling a silicone foam of 10 to 15 in magnification of foaming and 0.1 or less in specific gravity.

5. The figure adjusting pad as defined in claim 2, wherein said air-permeable hot melt comprises a spidery sheet-like member provided with a plurality of air holes and having a weight of 10 to 100 g/m$^2$.

6. The figure adjusting pad as defined in claim 2, wherein said knitted web is formed by subjecting at least one of a natural fiber and a chemical fiber to tricot stitch, raschel stitch, plain stitch, rib stitch or interlock stitch.

7. The figure adjusting pad as defined in claim 2, wherein said silicone gel layer is formed of a silicone gel having a material low in specific gravity added thereto.

8. The figure adjusting pad as defined in claim 2, and further comprising an air-permeable edging fabric arranged so that said pad body, facing sheet and backing sheet are bound-seamed together by said edging fabric around the periphery of said pad body.

9. The figure adjusting pad of claim 1, wherein said polyurethane film is formed of flexible polyurethane having a hardness within a range between 65° and 85° as defined by JIS-K6301.

10. The figure adjusting pad as defined in claim 9, wherein said foamed layer comprises an open-cell structure formed by pressing or crumpling a silicone foam of 10 to 15 in magnification of foaming and 0.1 or less in specific gravity.

11. The figure adjusting pad as defined in claim 10, wherein said air-permeable hot melt comprises a spidery sheet-like member provided with a plurality of air holes and having a weight of 10 to 100 g/m$^2$.

12. The figure adjusting pad as defined in claim 11, wherein said knitted web is formed by subjecting at least one of a natural fiber and a chemical fiber to tricot stitch, raschel stitch, plain stitch, rib stitch or interlock stitch.

13. The figure adjusting pad as defined in claim 11, wherein said silicone gel layer is formed of a silicone gel having a material low in specific gravity added thereto.

14. The figure adjusting pad as defined in claim 11, and further comprising an air-permeable edging fabric arranged so that said pad body, facing sheet and backing sheet are bound-seamed together by said edging fabric around the periphery of said pad body.

15. The figure adjusting pad as defined in claim 10, wherein said knitted web is formed by subjecting at least one of a natural fiber and a chemical fiber to tricot stitch, raschel stitch, plain stitch, rib stitch or interlock stitch.

16. The figure adjusting pad as defined in claim 10, wherein said silicone gel layer is formed of a silicone gel having a material low in specific gravity added thereto.

17. The figure adjusting pad as defined in claim 10, and further comprising an air-permeable edging fabric arranged so that said pad body, facing sheet and backing sheet are bound-seamed together by said edging fabric around the periphery of said pad.

18. The figure adjusting pad as defined in claim 9, wherein said air-permeable hot melt comprises a spidery sheet-like member provided with a plurality of air holes and having a weight of 10 to 100 g/m².

19. The figure adjusting pad as defined in claim 18, wherein said knitted web is formed by subjecting at least one of a natural fiber and a chemical fiber to tricot stitch, raschel stitch, plain stitch, rib stitch or interlock stitch.

20. The figure adjusting pad as defined in claim 18, wherein said silicone gel layer is formed of a silicone gel having a material low in specific gravity added thereto.

21. The figure adjusting pad as defined in claim 18, and further comprising an air-permeable edging fabric arranged so that said pad body, facing sheet and backing sheet are bound-seamed together by said edging fabric around the periphery of said pad body.

22. The figure adjusting pad as defined in claim 9, wherein said knitted web is formed by subjecting at least one of a natural fiber and a chemical fiber to tricot stitch, raschel stitch, plain stitch, rib stitch or interlock stitch.

23. The figure adjusting pad as defined in claim 9, wherein said silicone gel layer is formed of a silicone gel having a material low in specific gravity added thereto.

24. The figure adjusting pad as defined in claim 9, and further comprising an air-permeable edging fabric arranged so that said pad body, facing sheet and backing sheet are bound-seamed together by said edging fabric around the periphery of said pad body.

25. The figure adjusting pad as defined in claim 1, wherein said foamed layer comprises an open-cell structure formed by pressing or crumpling a silicone foam of 10 to 15 in magnification of foaming and 0.1 or less in specific gravity.

26. The figure adjusting pad as defined in claim 25, wherein said air-permeable hot melt comprises a spidery sheet-like member provided with a plurality of air holes and having a weight of 10 to 100 g/m².

27. The figure adjusting pad as defined in claim 26, wherein said knitted web is formed by subjecting at least one of a natural fiber and a chemical fiber to tricot stitch, raschel stitch, plain stitch, rib stitch or interlock stitch.

28. The figure adjusting pad as defined in claim 26, wherein said silicone gel layer is formed of a silicone gel having a material low in specific gravity added thereto.

29. The figure adjusting pad as defined in claim 26, and further comprising an air-permeable edging fabric arranged so that said pad body, facing sheet and backing sheet are bound-seamed together by said edging fabric around the periphery of said pad body.

30. The figure adjusting pad as defined in claim 25, wherein said knitted web is formed by subjecting at least one of a natural fiber and a chemical fiber to tricot stitch, raschel stitch, plain stitch, rib stitch or interlock stitch.

31. The figure adjusting pad as defined in claim 25, wherein said silicone gel layer is formed of a silicone gel having a material low in specific gravity added thereto.

32. The figure adjusting pad as defined in claim 25, and further comprising an air-permeable edging fabric arranged so that said pad body, facing sheet and backing sheet are bound-seamed together by said edging fabric around the periphery of said pad body.

33. The figure adjusting pad as defined in claim 1, wherein said air-permeable hot melt comprises a spidery sheet-like member provided with a plurality of air holes and having a weight of 10 to 100 g/m².

34. The figure adjusting pad as defined in claim 33, wherein said knitted web is formed by subjecting at least one of a natural fiber and a chemical fiber to tricot stitch, raschel stitch, plain stitch, rib stitch or interlock stitch.

35. The figure adjusting pad as defined in claim 33, wherein said silicone gel layer is formed of a silicone gel having a material low in specific gravity added thereto.

36. The figure adjusting pad as defined in claim 33, and further comprising an air-permeable edging fabric arranged so that said pad body, facing sheet and backing sheet are bound-seamed together by said edging fabric around the periphery of said pad body.

37. The figure adjusting pad as defined in claim 1, wherein said knitted web is formed by subjecting at least one of a natural fiber and a chemical fiber to tricot stitch, raschel stitch, plain stitch, rib stitch or interlock stitch.

38. The figure adjusting pad as defined in claim 37, wherein said silicone gel layer is formed of a silicone gel having a material low in specific gravity added thereto.

39. The figure adjusting pad as defined in claim 37, and further comprising an air-permeable edging fabric arranged so that said pad body, facing sheet and backing sheet are bound-seamed seamed together by said edging fabric around the periphery of said pad body.

40. The figure adjusting pad as defined in claim 1, wherein said silicone gel layer is formed of a silicone gel having a material low in specific gravity added thereto.

41. The figure adjusting pad as defined in claim 40, and further comprising an air-permeable edging fabric arranged so that said pad body, facing sheet and backing sheet are bound-seamed seamed together by said edging fabric around the periphery of said pad body.

42. The figure adjusting pad as defined in claim 41, and further comprising an air-permeable edging fabric arranged so that said pad body, facing sheet and backing sheet are bound-seamed together by said edging fabric around the periphery of said pad body.

* * * * *